United States Patent [19]
Hollingshead et al.

[11] 3,934,583
[45] Jan. 27, 1976

[54] THERAPEUTIC MUSCULOSKELETAL SUPPORT SLEEVE AND METHOD OF MANUFACTURING SAME

[75] Inventors: Donald W. Hollingshead; Cecil E. Phillips, both of Eugene, Oreg.

[73] Assignee: Danny W. Hollingshead, Eugene, Oreg.

[22] Filed: Sept. 27, 1974

[21] Appl. No.: 509,821

[52] U.S. Cl. ................ 128/165; 128/80 C; 128/77
[51] Int. Cl.² ......................................... A61F 13/00
[58] Field of Search .......... 128/165, 80 C, 80 R, 87, 128/77, 166; 2/22, 24

[56] References Cited
UNITED STATES PATENTS

| | | | |
|---|---|---|---|
| 2,858,540 | 11/1958 | Morrison | 128/80 C |
| 3,046,981 | 7/1962 | Biggs, Jr. et al. | 128/80 C |
| 3,074,400 | 1/1963 | Schulman | 128/165 |
| 3,092,110 | 6/1963 | Duensing | 128/165 X |
| 3,463,147 | 8/1969 | Stubbs | 128/165 X |
| 3,473,527 | 10/1969 | Spiro | 128/165 X |
| 3,785,371 | 1/1974 | Lewis | 128/165 X |
| 3,786,804 | 1/1974 | Lewis | 128/80 C |
| 3,804,084 | 4/1974 | Lehman | 128/165 X |

*Primary Examiner*—Robert W. Michell
*Assistant Examiner*—J. Yasko
*Attorney, Agent, or Firm*—Chernoff & Vilhauer

[57] ABSTRACT

A flexible therapeutic anatomical support of form-fitting, compressive, heat-retaining elastic foam material, the supportive, compressive and movement-resisting forces of which are selectively reinforced and relieved, for supporting, protecting and resisting the movement of the muscles and skeletal structure at joints and other limb areas during pre-surgery conditioning, post-trauma, and post-surgery convalescence. A limb-ensheathing sleeve of sufficient length to cover the affected portion of the lib is fabricated from a sheet of foam neoprene material bent around to form a tube and adhesively secured at its seam edges with contact cement. The sleeve is configured according to measurements taken from the actual limb or joint after such measurements have been suitably modified to ensure that the resulting sleeve will provide the desired amount of support and compression. Selective reinforcement of the supportive, compressive and movement-resisting forces of the support sleeve is achieved by the securement of a plurality of elastic-fabric-backed strips of elastic foam material to the inside and outside surfaces of the sleeve by adhesive attachment thereto while the strips are either in a relaxed state or held in tension, as desired. Selective relief is achieved by removing a portion of the support sleeve material over the area of the limb to be relieved and either leaving the relieved area exposed or covering the opening with a patch of elastic-fabric-backed elastic foam material adhesively-attached to the outside surface of the sleeve. The sleeve support can be readily removed by the wearer for cleaning or treatment of the afflicted joint or limb and reapplied, as oftentimes as necessary.

10 Claims, 18 Drawing Figures

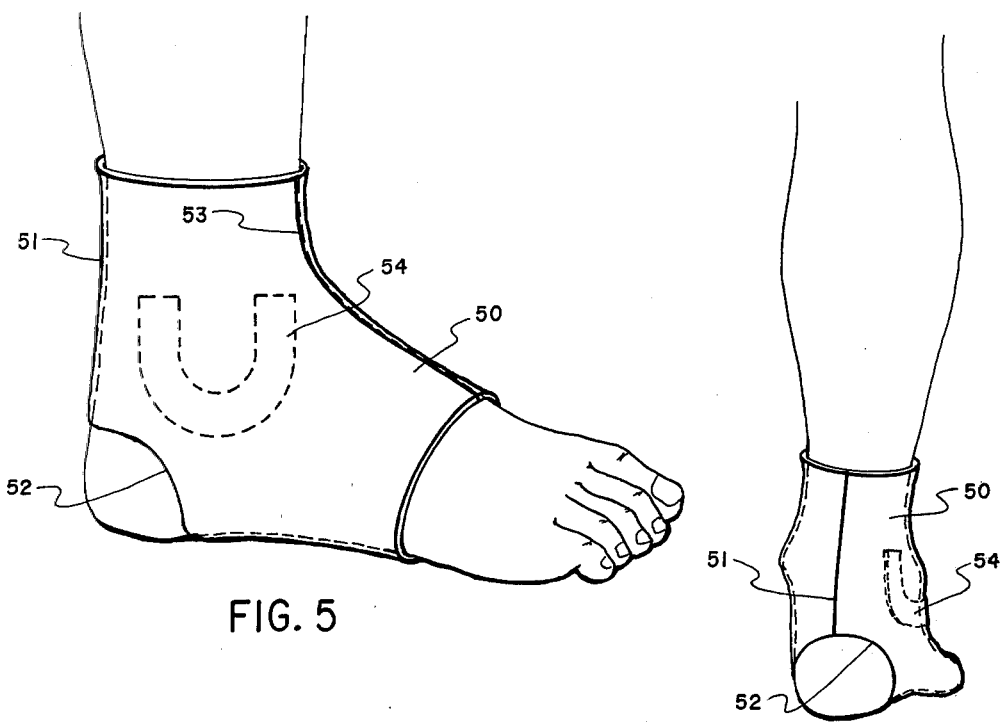
FIG. 5
FIG. 6
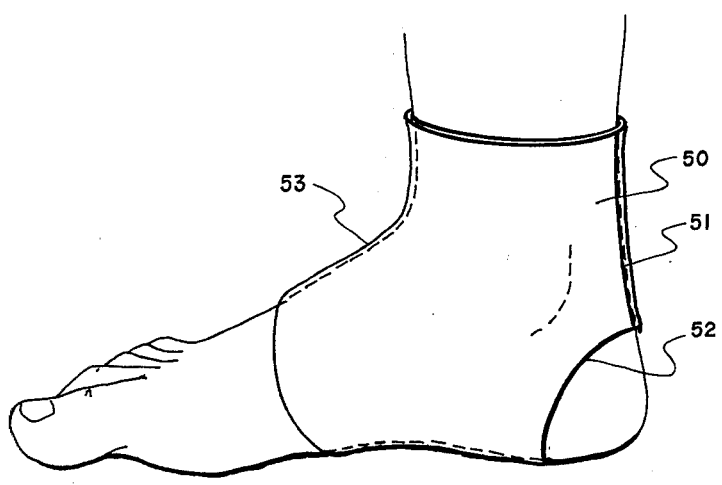
FIG. 7
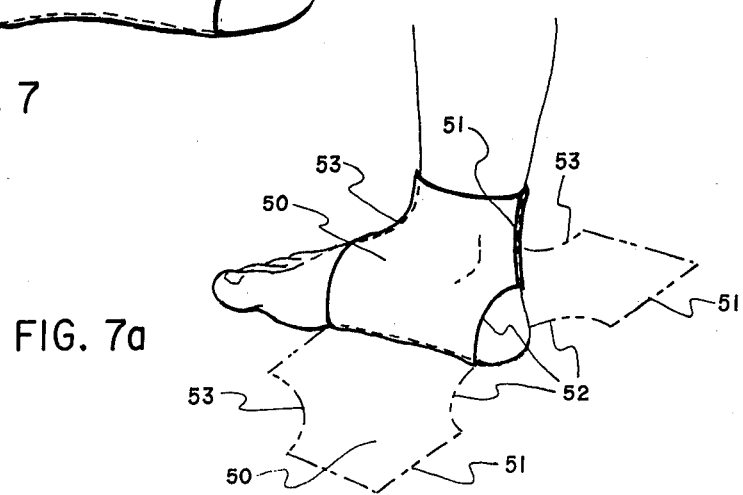
FIG. 7a

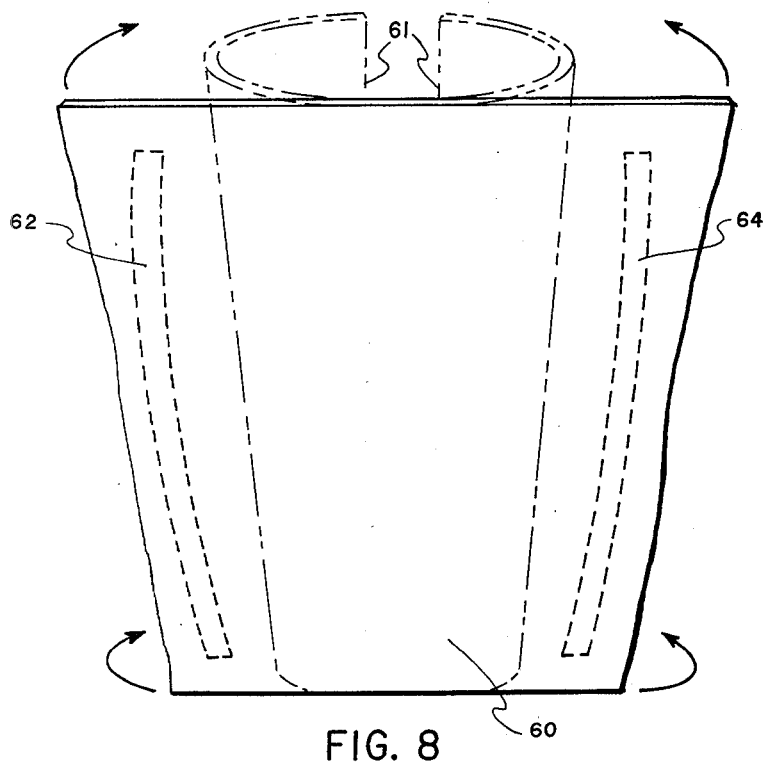
FIG. 8
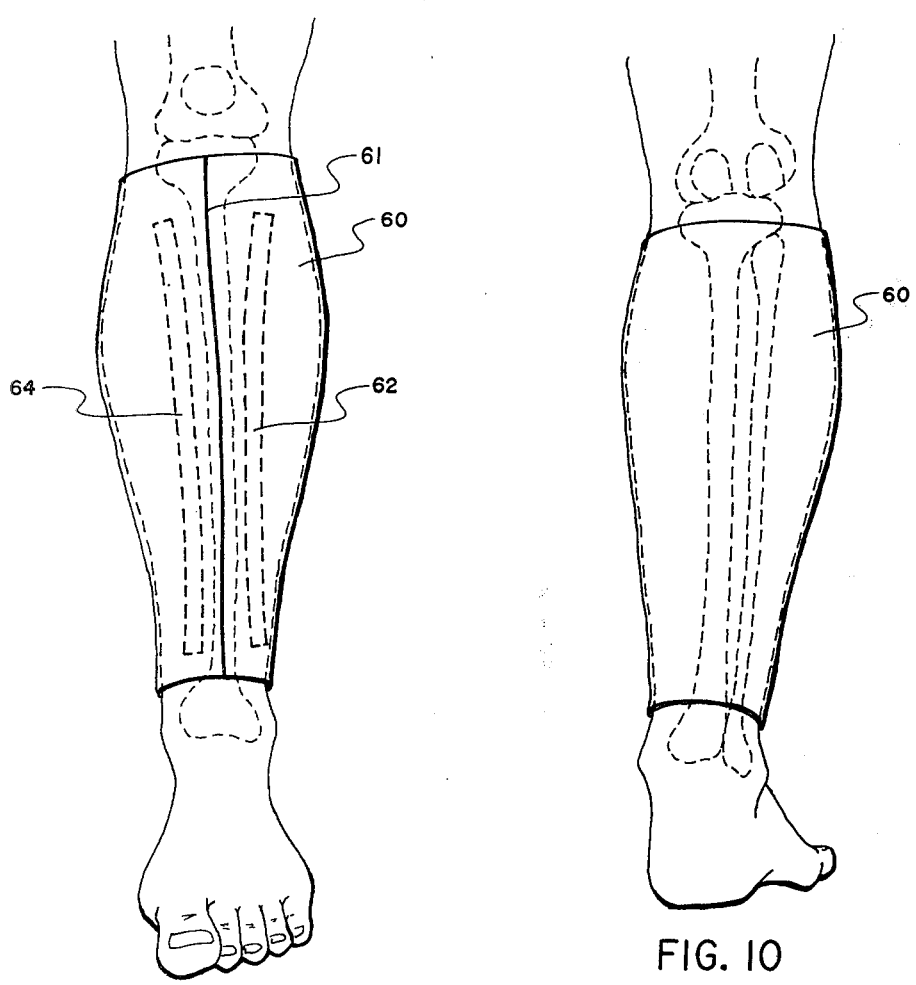
FIG. 9
FIG. 10

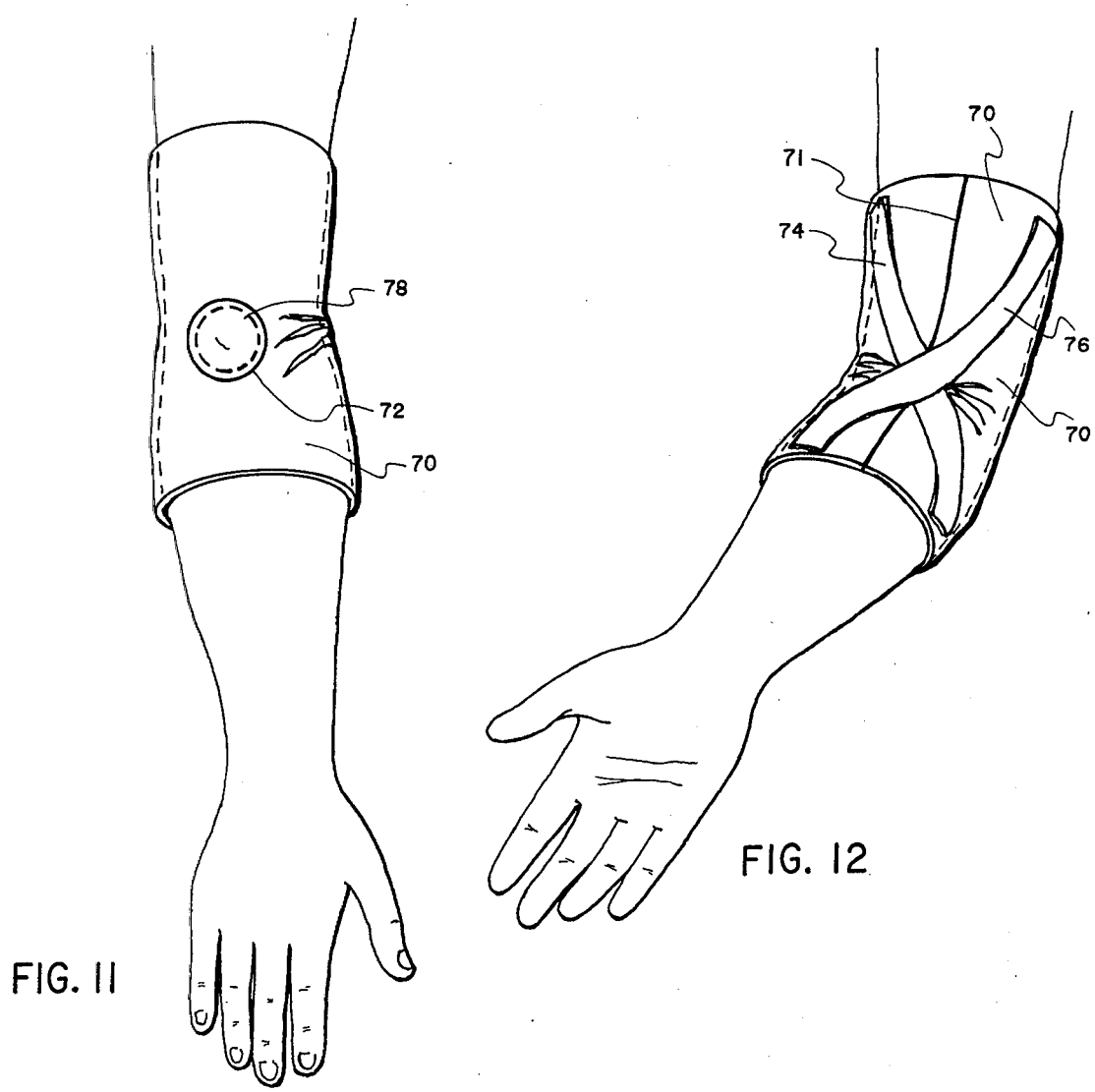
FIG. 11
FIG. 12
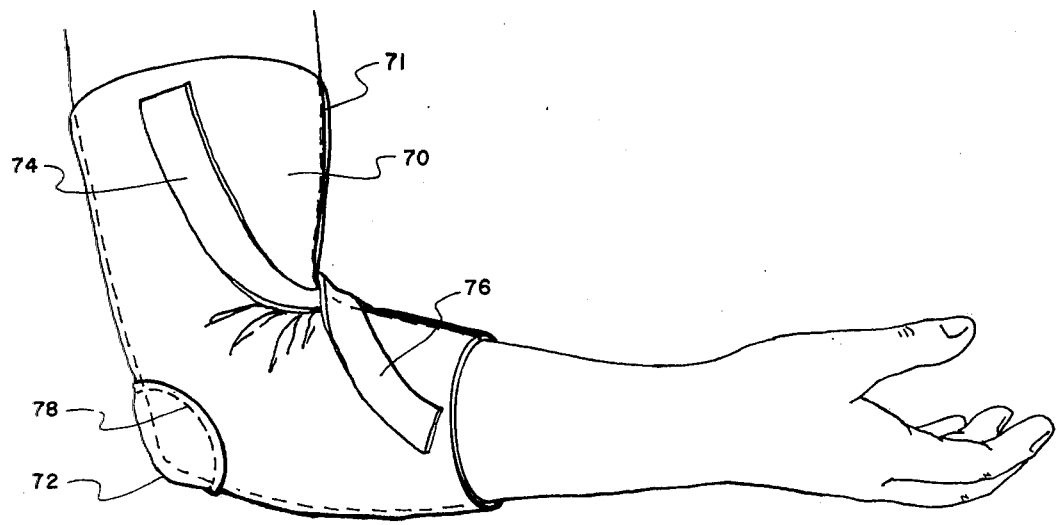
FIG. 13

THERAPEUTIC MUSCULOSKELETAL SUPPORT SLEEVE AND METHOD OF MANUFACTURING SAME

BACKGROUND OF THE INVENTION

The present invention relates to a therapeutic anatomical support of the type generally used to apply pressure around and about a portion of a limb to reduce swelling and to provide protection and support during the convalescent period following joint surgery or joint trauma and during the treatment of shin splints.

One of the most common types of limb trauma is the sprain, usually defined as any strain-induced injury to a joint that results in a possible ligament or tendon rupture, but does not cause any skeletal dislocation or fracture. Sprains are especially common at the knee and ankle joints because of their locomotive and weight-bearing functions and occur almost as frequently at the joint of the elbows and wrists. They are usually followed by a significant amount of swelling due to diffusion (escape of fluid into a tissue or cavity) and edema (excessive accumulation of water fluids in the tissue spaces). Although the initial treatment of joint sprains necessarily varies with the severity of the sprain, the final phase of treatment usually includes the application and prolonged wearing of some type of protective, supportive and movement-resisting wrapping around the affected joint. It is not uncommon, even with moderate sprains, for this wrapping to be worn for a period of several weeks or months.

A common type of limb trauma occurring away from a joint is that where a muscle of the lower leg is torn from the side of the tibia or shin bone. This type of injury, referred to non-medically as a shin splint, occurs most often among skiers and basketball players and its treatment includes the application of a compressive wrapping to hold the affected muscle against the bone.

Several means have been devised for applying supportive pressure around and about a joint or other affected limb area. These include the application of adhesive tape, either as a single long strip or as a number of shorter strips, such as the commonly used Gibney ankle strapping consisting of fifteen individual adhesive strips, each of a different length; successively wrapping the affected area with a single strip of elastic material, such as that utilized in Hoey U.S. Pat. No. 3,805,781; and ensheathing the affected area in elastic or non-elastic sleeves of various shapes, sizes, and materials.

One of the main disadvantages of these conventional types of compressive limb supports, especially those formed from single or multiple strips of adhesive tape, is that, to ensure correct support and movement resistance, they must be applied by a physician or other medically-skilled person. Even then, it is difficult to achieve selective pressure differentials along the length of the support because of the difficulty in controlling the tension in the tape as it is wrapped around the limb and, therefore, almost impossible to predetermine the supportive and compressive result with any degree of accuracy. The use of a number of strips of adhesive tape rather than a single long strip, affords some selective reinforcement, but since the tape is usually non-elastic, the result is selective support and movement resistance, but not selective compression.

Also, an adhesive-tape support, once it is removed, must still be reapplied by an expert and, therefore, cannot be readily removed and reapplied in the home for purposes of bathing and massaging the injured limb.

The substitution of a long strip of elastic material for the adhesive tape results in a limb support whose compressive force is easier to control as the strip is applied by varying the amount of tension on the strip as it is wound around the limb, but the effect of this control is impossible to accurately predetermine. In addition, the requirement for an expert to properly apply the strip is not eliminated. The patient must still return to the physician's or therapist's office each time the support is to be removed and reapplied.

Non-elastic sleeves, even those capable of being selectively reinforced by inserting a rigid support member into an external pocket sewn into the outer surface of the sleeve, are useful mainly for support and not for compression. Sleeves of elastic material have been used to provide both compression and support, however, until now no means have been disclosed to effectively predetermine the amount of compressive force applied at any given point or area around the ensheathed portion of the injured limb or to effectively predetermine the amount of joint movement resistance provided by the sleeve.

Summary of the Present Invention

The present invention is directed to a non-rigid support sleeve of the type formed from a flexible material and used to apply supportive and compressive forces around and about an injured portion of a limb or joint, and, more particularly, to a form-fitted elastic sleeve of compressive, heat-retaining material, the compressive and movement-resisting force of which may be selectively reinforced and relieved by specific predetermined amounts at specific predetermined points around and about the affected portion of the limb or joint.

At least four basic embodiments of the support sleeve are envisioned; one for the knee, ankle, lower leg and elbow. Each comprises as its base an individually-fitted sleeve formed from an elastic foam material, such as foam rubber or neoprene similar to that conventionally used in a diver's wet-suit. By using an elastic foam material, both compression and heat retention are achieved, the latter being especially important and beneficial not only for the diminution of effusion and the reduction of edema, but also as an aid for conditioning the tissue prior to surgery when surgery is necessary. The circumferential dimensions for the different support sleeves are determined by taking measurements around the affected portion of the actual limb or joint and then reducing those measurements by an amount calculated to produce the desired compression differential at each point along the sleeve. For example, the basic knee support would not only be generally formed to start at mid-calf, taper in toward the knee and then taper out toward mid-thigh, but also to taper at rates greater or lesser than those necessary to conform to the shape of the knee, thereby varying the resultant compression by predetermined amounts along the length of the support. Once the basic measurements have been taken and modified as indicated above, a pattern is cut from a sheet of the elastic foam material and formed into a tubular configuration by bending the two appropriate opposing edges of the pattern around until they meet one another. The seam created where the two edges of the pattern come together is formed by adhesively attaching the two edges to one another with contact cement. To facilitate walking while wearing the support sleeve, a portion of the sleeve material directly behind the knee may be removed before or after the seam is formed, thereby relieving the compression, reducing the movement resistance and allowing the knee and the support sleeve to be more readily flexed.

With minor knee sprains, the application of the basic support sleeve, extending from a few inches below the knee to a few inches above, may be adequate to provide the necessary support, warmth and edema reduction. However, as the nature of the injury departs from a minor sprain, modifications to the basic sleeve may be necessary. In the case of patellar chondromalacia, a condition where the cartilage of the articular or underneath surface of the patella becomes roughened and causes pain when the knee is flexed or extended under a load, a portion of sleeve material roughly the size and shape of the patella is removed directly over the patella to relieve the pressure thereon. To protect the patella thus exposed, and also to maintain the compressive integrity of the sleeve, a piece of material similar to that used for the sleeve, either plain or elastic-fabric-backed for decreased elasticity, can be adhesively attached over the relieved area as a protective patch. If patellar instability is present, a similar area of sleeve material is removed over the patella, but the resultant aperture is encircled by a ring, also of elastic foam material, that is adhesively attached to the interior surface of the sleeve before the protective patch is applied. The addition of the ring serves to reinforce the aperture and offer increased resistance to patellar movement, thereby enhancing patellar stability.

Where the injury to the knee is sufficient to cause anteroposterior instability, a tendency of the knee joint to flex voluntarily, a pair of pretensioned, external elastic bands or strips of either plain or elastic-fabric-backed foam material are adhesively attached to the sleeve such that each strip begins at the upper rear of the sleeve, extends around opposite sides of the knee joint and down across the front, crosses the other strip just below the patellar relief aperture, and terminates at the lower rear of the support. The crossing strips are pretensioned by being stretched a predetermined percent of their at-rest length and held thus while being adhesivedly attached to the sleeve. The contraction of the strips, once the tension is released, increases the elastic resistance of the sleeve along the length of the strip, thereby offering an increased resistance to flexion of the knee joint.

The ankle support comprises a form-fitted, boot-like sleeve, the top of which extends above the ankle and the bottom of which extends about midway between the heel and the toes of the foot. An additional opening is cut around the heel to minimize the resistance to flexion and extension of the ankle joint. In cases where the sprain was caused by hyper-eversion, or an outward bending of the ankle joint, a U-shaped band of elastic foam material may be attached to the interior surface of the sleeve just below and partially surrounding the malleolus of the fibular to provide extra support and protection where swelling is most likely to occur.

The support envisioned for the treatment of shin splints comprises a form-fitted sleeve that extends from just above the ankle to just below the knee. A pair of elastic foam material strips are attached to the interior surface of the sleeve along the front of the support sleeve, parallel with the longitudinal axis of the leg and spaced on either side of the tibia, to increase elastic resistance and further compress the lower front leg muscles against the bone.

The elbow support is similar to that for the knee and comprises a form-fitted sleeve extending from midway up the lower arm to midway up the upper arm. This support is beneficial for the treatment of mild sprains and strains; especially the afflication commonly known as "tennis elbow," a condition where the tendinous insertion of the wrist extensor muscles have been strained or become affected by rheumatic inflammation such that strong contraction of the hand causes pain and results in a weakened grip. This latter condition is so named because of its frequent occurance among tennis players, but it can also follow joint trauma from other activities. To ease the tension on the extensor muscles, the elbow joint may be supported in a slightly flexed position by the external attachment of a pair of pretensioned elastic strips or bands applied as a cross over the surface of the sleeve at the inside of the elbow joint. The increased tension provided by these strips will tend to prevent the sleeve, and thereby the elbow joint, from being involuntarily completely extended.

If desirable, a portion of the elbow sleeve material can be removed over the upper end of the ulna, at the point where the tricep has its insertion, to ease the compression there and to facilitate flexion of the elbow joint. For protection of the ulna, and to maintain compressive integrity, an external patch may be applied to the sleeve over the area thus exposed.

Once any of the envisioned sleeves has been tailored, constructed, fitted and adjusted by one experienced in the art, it may be removed and reapplied by the wearer without further expert attention, thereby allowing the injured limb to be bathed and massaged at home without the need to return to the physician's or therapist's office to have the support reapplied.

Although support sleeve embodiments have been described for application to the knee, ankle, lower leg and elbow, additional embodiments could also be designed for other portions of the limbs as well, e.g., the upper arm or leg, the lower arm or the wrist.

It is, therefore, a primary objective of the present invention to provide a therapeutic limb and joint support, the compressive force of which may be varied by predetermined amounts over the area of the limb to be supported.

It is a secondary objective of the present invention to provide a therapeutic limb and joint support, the compressive force of which can be relieved or reinforced at predetermined points over the area of the limb to be supported.

It is an additional objective of the present invention to provide a therapeutic limb and joint support capable of capturing and retaining the body heat around and about the area of the limb being supported.

It is a further objective of the present invention to provide a therapeutic limb and joint support capable of resisting the movement of a joint being supported by a predetermined amount in a predetermined direction.

It is a still further objective of the present invention to provide a therapeutic limb and joint support that is manufactured by cutting an individually tailored pattern from a sheet of elastic foam material, forming said pattern into a tubular configuration and adhesively joining the two appropriate opposed edges of the pattern to one another.

It is a primary advantage of the present invention that, once initially fitted, the therapeutic limb and joint support may be removed and reapplied without the need for additional expert assistance.

It is a primary feature of the present invention that the elastic foam material of the therapeutic limb and joint support provides substantial protection against subsequent injury to the limb being supported.

The foregoing objectives, features and advantages of the present invention will be more readily understood upon consideration of the following detailed description of the invention taken in conjunction with the accompanying drawings.

BRIEF DESCRIPTION OF THE DRAWINGS

FIG. 5 is a lateral view of the ankle support embodiment of the present invention.

FIG. 6 is a posterior view of the ankle support embodiment of the present invention.

FIG. 7 is a medial view of the ankle support embodiment of the present invention.

FIG. 7a is a partially-phantomed perspective view of the ankle support embodiment of the present invention.

FIG. 8 is a partially-phantomed elevation of the shin support embodiment of the present invention.

FIG. 9 is an anterior view of the shin support embodiment of the present invention.

FIG. 10 is a posterior view of the shin support embodiment of the present invention.

FIG. 11 is a posterior view of the elbow support embodiment of the present invention.

FIG. 12 is an anterior view of the elbow support embodiment of the present invention.

FIG. 13 is a lateral view of the elbow support embodiment of the present invention.

DESCRIPTION OF THE PREFERRED EMBODIMENT

Referring to FIGS. 1 through 4, the knee support embodiment of the present invention is seen to comprise a joint-ensheathing sleeve 20, extending from about four inches below the knee to about five inches above, and completely surrounding the knee, except for a substantially elliptical aperture 22 about halfway up the back of the sleeve. Aperture 22, located directly behind the knee joint and measuring approximately 5½ inches by 2¾ inches, is formed to facilitate flexion of the knee joint and to minimize any chafing that might result from the sleeve rubbing against the skin when the sleeve is worn for long periods of time.

Sleeve 20 is formed from a single sheet of ¼ inch, smooth-sided, elastic, foam neoprene formed into a generally tubular shape and the seam edges secured together by an adhesive cement. The dimensions of the sleeve are determined by the size of the knee to be supported and the purpose for which the sleeve is to be worn. The circumference of the patient's leg is measured at 3 points; 5 inches above the knee, at the knee, and 4 inches below the knee. Then, if the sleeve is to be worn to reduce swelling, these measurements are reduced by 1½ inches, 1 inch, and 1½ inches, respectively. If swelling is not present and the sleeve is to be worn for support only, the same basic measurements are reduced by 1¾ inches, 1½ inches, and 1¾ inches, respectively. These measurement modifications are typical for an average adult leg and are not meant to indicate the proper reduction for all cases. Correct fitting of the knee support is an individual process and necessarily involves a certain amount of trial and error as the fitter gains expertise.

The preferred elastic foam material is similar to that conventionally used in a diver's wet-suit and is favored because of its elasticity, its cushioning ability and its heat-retaining characteristics. A typical elastic foam material found to be satisfactory is that manufactured by Rubatex Rubber Co., of Bedford, Virginia, under the designation G231N 1/4 S2S, where the S2S indicates that both surfaces of the material are smooth rather than exposed foam. This material not only provides the desired compression and protection, but its ability to capture and retain body heat increases the effectiveness of the sleeve in reducing swelling. The preferred adhesive for permanently bonding the seam edges of the neoprene sleeve material together is a G231 liquid neoprene adhesive such as that marketed under the trademark "Black Magic" by Aqua-Craft Co., of San Diego, Calif.

Figure 4A:
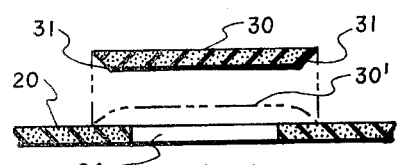
FIG. 4a is a detail sectional view taken along line 4a—4a of FIG. 4.

Referring again to the Figures, the knee support is seen to further comprise a second smaller aperture 24 formed in the front of sleeve 20 at a point directly over the patella. This aperture is formed when it is desired to relieve the compressive force applied to the patella as, for example, when patellar chondromalacia is present. To protect the patella thus exposed and to maintain the compressive integrity of the sleeve across aperture 24, a circular patch 30 of nylon-backed elastic foam material is adhesively attached to the exterior surface of sleeve 20 around aperture 24 in such a manner as to completely cover the aperture. As shown in the detail view of FIG. 4a, the peripheral edge 31 of patch 30 is beveled at a 45 degree angle so that when the patch is glued to the sleeve, the edge can also be glued down to create a smooth surface around the patch.

Figure 4B:
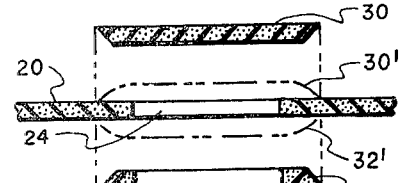
FIG. 4b is an alternate detail sectional view taken along line 4b—4b of FIG. 4.

In some cases, for example, as treatment for patellar instability, it may be desirable, before attaching patch 30, to reinforce aperture 24 with an internally-attached, elastic foam ring 32, as shown in detail in FIG. 4b. As with patch 30, the peripheral edge 33 of ring 32 is beveled at 45 degree angle and glued down to provide a smooth surface at its boundary with sleeve 20. Patch 30 is attached over aperture 24 in the same manner as before.

The material used to form patch 30 and ring 32 is similarly available from Rubatex Rubber Co. under the designation G231N 1/4 S1S N1S indicating one smooth side and one nylon-backed side, and the glue used to attach patch 30 and ring 32 to sleeve 20 is G231 liquid neoprene adhesive.

Figure 1:
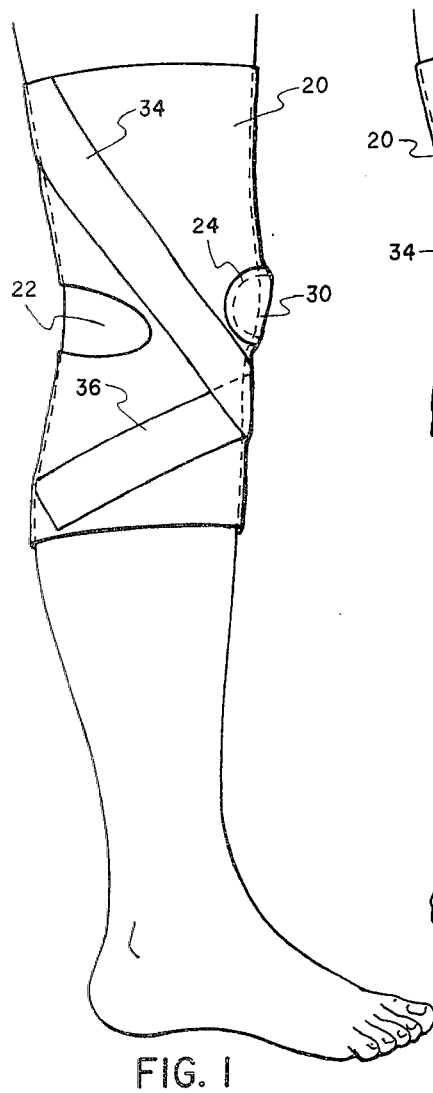
FIG. 1 is a lateral view of the knee support embodiment of the present invention.
Figures 2, 2A:
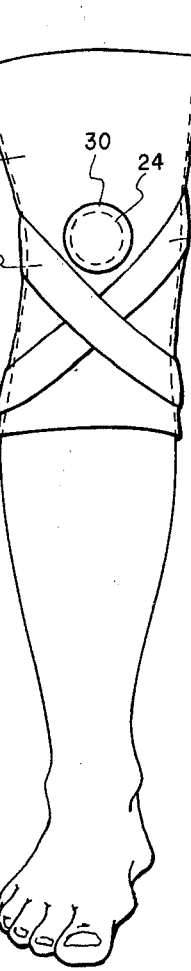
FIG. 2 is an anterior view of the knee support embodiment of the present invention.
FIG. 2a is an anterior view of an alternate knee support embodiment of the present invention.
Figure 3:
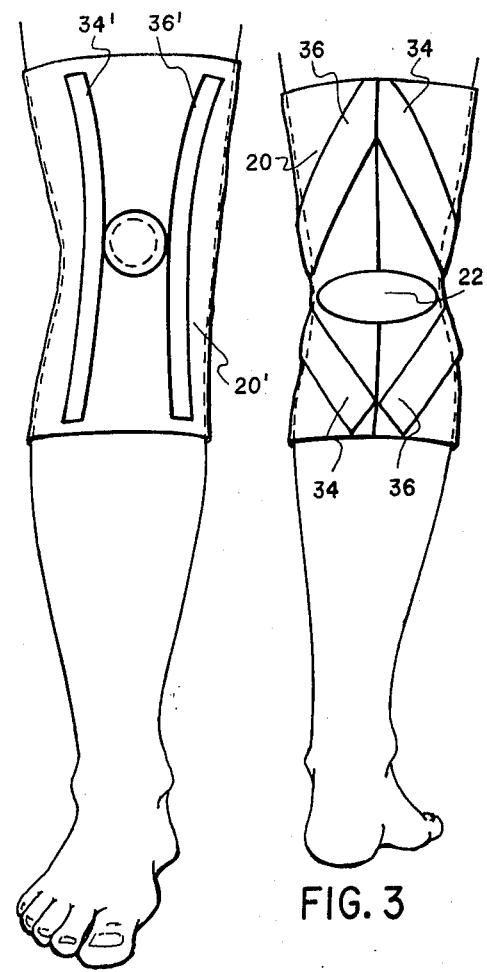
FIG. 3 is a posterior view of the knee support embodiment of the present invention.
Figure 4C:
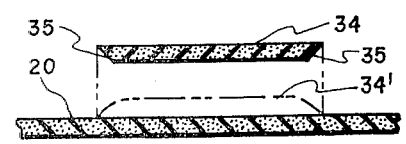
FIG. 4c is a detail sectional view taken along line 4c—4c of FIG. 4.

As shown in the Figures, the knee support may also include two ½ to ¾ inch wide, adhesively-attached crossing strips 34 and 36 of a nylon-backed foam material similar to that used for patch 30 and ring 32. Strip 36 starts at the upper left rear of sleeve 20, extends down across the front just below aperture 24, and terminates at the lower right rear of the sleeve. Strip 34 starts at the upper right rear of sleeve 20, extends similarly down across the front, crosses strip 36 just below aperture 24, and terminates at the lower left rear of the sleeve. These nylon-back strips 34 and 36, which have decreased elasticity as compared to their smooth-sided counterparts, are employed to provide increased resistance to flexing movement of the knee joint. Additional resistance may be achieved by holding strips 34 and 36 under tension as they are attached so that their contraction upon release will further increase the resistance of sleeve 20 to flexing motion. As shown in FIG. 4c, the edges 35 of strips 34 and 36 may also be beveled at a 45 degree angle as were the edges of patch 30 and ring 32. (Although strips 34 and 36 are shown in the Figures as crossing at the front of sleeve 20, they could alternatively be located as shown in FIG. 2a. This placement would increase the resistance of the sleeve to flexing movement, while decreasing the resistance to medial and lateral motion.)

Figure 4:
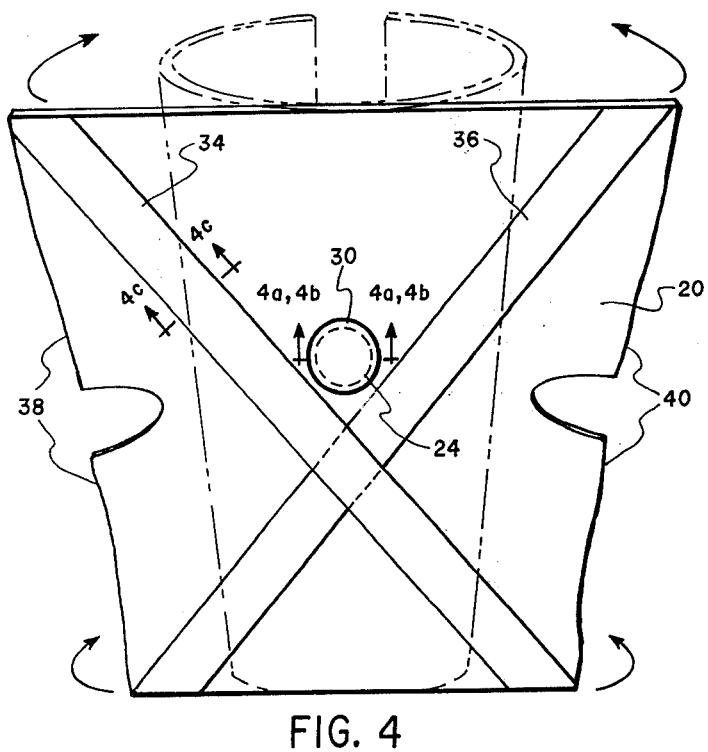
FIG. 4 is a partially-phantomed elevation of the knee support embodiment of the present invention.

To construct the knee support, sleeve 20 is cut from a sheet of foam material, as indicated in FIG. 4, according to the dimensions calculated as described earlier and apertures 22 and 24 are formed. Patch 30, ring 32, and strips 34 and 36 may be attached before the two side edges of the sleeve are joined or after. In either case, sides 38 and 40 are coated with four successive coats of G231 liquid neoprene adhesive applied at about three minute intervals. When the last coat is dry to the touch, the edges are placed in contact with each other and pinched together. The contact-cement-type action of the adhesive will form an instant and permanent water-and-detergent-proof bond between the edges thus joined, thereby converting the sheet of foam material into the tubular sleeve 20. Patch 30, ring 32, and strips 34 and 36 are similarly attached by coating all surfaces to be joined with the adhesive and bringing the surfaces into contact when the adhesive has become dry to the touch. The use of a contact-type adhesive is especially critical when attaching strips 34 and 36 under tension and when affixing the beveled edges of the patch, ring, and strips.

Before each use the knee support is washed in soap and water, rinsed, and air-dried to remove any bacteria and perspiration left from the last use, thereby minimizing the risk of skin irritation. If the support is not fitted too tightly, it may be simply pulled over the foot and up to the knee. Otherwise, it may be necessary to coat the leg with a lubricating powder or gel to enable the support to be pulled over the foot and up to the knee. In case of exceptional swelling where the fit is especially tight, a portion of the sleeve may be rolled inside out like a sock to facilitate its positioning over the knee. A similar procedure would be used to remove the support in order to permit the knee to be massaged and washed.

The ankle support embodiment of the present invention, shown in FIGS. 5 through 7, comprises a form-fitted, boot-like sleeve 50 of elastic foam material cut from a single sheet and bonded with adhesive at seam 51 and 53 as indicated in FIG. 7a or formed as a molded one-piece article. Sleeve 50 extends from midway between the toes and the heel of the foot to above the ankle and the material used, dimension calculation, and seam gluing process are similar to that described for the knee support. Heel aperture 52 is formed to facilitate flexion and extension of the ankle joint and its size and shape are determined by the amount of movement restriction desired. U-shaped strip 54 of nylon-backed foam material is adhesively attached in a relaxed condition to the interior surface of the lateral side of sleeve 50 to partially surround the malleous of the fibula and to increase the compressive force therearound. This is especially therapeutic in those cases where the ankle has been sprained by an excess outward-bending movement. The edges of U-shaped strip 54 may either be beveled as were the strips of the knee support or left perpendicular as shown in the Figures.

The shin splint support embodiment of the present invention, shown in FIGS. 8 through 10, comprises sleeve 60 and two ½ inch wide nylon-backed foam strips 62 and 64. Sleeve 60 is formed, as was the knee support sleeve, from a sheet of ¼ inch elastic foam neoprene, as indicated in FIG. 8, and its side edges are similarly joined by adhesive at seam 61. Strips 62 and 64 are adhesively attached in a relaxed condition along the interior of the front of sleeve 60 about ¼ to ½ inch from the center of the tibia and parallel with the longitudinal axis of the leg. Their purpose here is not to resist movement, but to increase the compressive force of the sleeve along the front of the tibia, thereby pressing the lower front leg muscles against the bone. The edges of strips 62 and 64 may be beveled or perpendicular depending upon the smoothness desired at the juncture between the strips and the sleeve.

Lastly, the elbow support embodiment of the present invention, shown in FIGS. 11 through 13, is seen to comprise sleeve 70, adhesively-secured seam 71, patch 72, and strips 74 and 76. To decrease the resistance of the sleeve to flexing motion and to decrease the compression on the tip of the elbow, aperture 78, with a diameter of around 1½ inches, may be formed as indicated in FIGS. 11 and 13. Patch 72, similar to patch 30 of the knee support is used to protect the portion of the elbow thus exposed and to maintain the compressive integrity of the sleeve. In those cases where it is desirable to maintain the elbow in a slightly flexed position, nylon-backed foam strips 74 and 76 may be adhesively attached in a cross-like manner across the inside of the elbow joint, as shown in FIG. 12, to resist the extending movement of the lower arm. Increased resistance can be achieved by attaching the strips while they are held under tension. The materials used and the construction techniques employed for the elbow support are similar to those described for the knee support.

Although only four embodiments of the present invention have been described, it is obvious that additional embodiments are possible without departing from the concept of the invention, such as supports for the lower arm or the wrist. In addition, similar support sleeves could be fashioned and employed as therapeutic devices for the treatment of sprains and strains in the limbs of animals, for example, horses and cattle.

The terms and expressions which have been employed in the foregoing abstract and specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A musculoskeletal shin support device comprising:
   a. an elongate form-fitted sleeve of elastic, heat-retaining foam material adapted to extend from above the ankle to below the knee for compressively ensheathing the area around and about the lower leg; and
   b. a plurality of elongate elastic strips adhesively attached in a relaxed condition along their entire lengths to the interior surface of said sleeve and spaced substantially anterior and parallel to the longitudinal axis of said sleeve in positions so that, when said sleeve is fitted in place about the lower leg, the elastic strips will not resist movement, but will increase the compressive force of the sleeve and press the anterior muscles of the lower leg against the tibia.

2. A musculoskeletal knee support sleeve for supporting the tissues and bones of the leg around and about the knee joint comprising:
   a. a form-fitted sleeve of elastic, heat-retaining foam material, extending from above the knee joint to below the knee joint, for compressively ensheathing the area around and about said knee joint; and
   b. a plurality of elongate strips of elastic foam material attached along their entire lengths to the outer surface of said sleeve and extending substantially from the top to the bottom of said sleeve, said strips being in tension relative to said sleeve whereby said tensioned strips serve to reinforce said sleeve and increase its resistance to flexing motion of the knee.

3. The knee support of claim 2 wherein one of said elastic strips extends from the upper rear of said sleeve, down around one side and across the front of said sleeve, and another of said strips extends from the upper rear of said sleeve, down around the other side and across the front of said sleeve, both of said strips terminating at the lower rear of said sleeve.

4. The knee support of claim 3 further comprising means defining a patella-sized aperture in the surface of said sleeve anterior and proximate said knee joint when said support sleeve is fitted in place, said aperture serving to relieve the compressive force of said sleeve over the patella, and wherein said elastic strips extending across the front of said sleeve are positioned below said aperture means.

5. The knee support of claim 4 further comprising a patch of elastic foam material adhesively attached to the exterior surface of said sleeve and covering said aperture to maintain the compressive integrity of said sleeve across said aperture and to protect the patella from contact injury.

6. The knee support of claim 4 further comprising a reinforcing border of elastic foam material adhesively attached to the interior surface of said sleeve around said aperture to reinforce the material of said sleeve and thereby maintain the compressive integrity of said sleeve across said aperture.

7. The knee support of claim 2 wherein one of said elastic strips extends along either side of and proximate the front of said sleeve.

8. A musculoskeletal knee support comprising:
   a. a form-fitted sleeve of elastic, heat-retaining foam material, extending above and below the knee joint, for compressively ensheathing the area around and about said knee joint; and
   b. a plurality of elongate strips of elastic material adhesively attached along their entire length to the surface of said sleeve, the material of said strips being in tension relative to the material of said sleeve.

9. A method of manufacturing a custom-fitted musculoskeletal knee support sleeve for supporting the tissue and bone structure of the leg around and about the knee joint comprising the steps of:
   a. measuring the leg to be supported to obtain a first circumferential measurement above the knee, a second circumferential measurement at the knee, and a third circumferential measurement below the knee;
   b. decreasing each of said circumferential measurements by respective predetermined amounts;
   c. cutting an approximately trapezoidal pattern having two substantially mutually parallel edges from a sheet of elastic, heat-retaining foam material with the length of one of said parallel edges of said pattern substantially equal to said decreased first circumferential measurement, the length of the other of said parallel edges of said pattern substantially equal to said decreased third circumferential measurement, and the length of a width dimension located approximately mid-way between and parallel to said mutually parallel edges substantially equal to said decreased second circumferential measurement;
   d. attaching a pair of elongate strips of elastic material from corner to corner diagonally across said pattern;
   e. forming said pattern into a substantially tubular sleeve configuration by bending the two non-parallel edges of said approximately trapezoidal pattern around until they come together; and
   f. adhesively joining said non-parallel edges to one another to form a seam along the length of said sleeve.

10. The method of claim 9 wherein said step (d) includes holding said elastic strips in tension while attaching said strips along their entire length to said pattern.

* * * * *